(12) United States Patent
Huerland et al.

(10) Patent No.: US 6,843,251 B1
(45) Date of Patent: Jan. 18, 2005

(54) BALLOON FOR PREPARING FOR AND EASING HUMAN BIRTH

(75) Inventors: Thomas Huerland, Germering (DE); Robert Ibler, Olching (DE); Gregor Tuma, Munich (DE)

(73) Assignee: TECSANA GmbH, Munich (DE)

(*) Notice: Subject to any disclaimer, the term of this patent is extended or adjusted under 35 U.S.C. 154(b) by 253 days.

(21) Appl. No.: 10/088,754

(22) PCT Filed: Sep. 20, 2000

(86) PCT No.: PCT/EP00/09207

§ 371 (c)(1),
(2), (4) Date: Mar. 20, 2002

(87) PCT Pub. No.: WO01/21080

PCT Pub. Date: Mar. 29, 2001

(30) Foreign Application Priority Data

Sep. 20, 1999 (DE) ............................. 199 45 050

(51) Int. Cl.[7] .............................. A61G 15/00
(52) U.S. Cl. ............ 128/845; 604/103.7; 604/279
(58) Field of Search ............... 128/845, 846; 604/103.7, 279

(56) References Cited

U.S. PATENT DOCUMENTS

| 4,018,230 A | 4/1977 | Ochiai et al. |
| 4,338,943 A | 7/1982 | Okamoto et al. |

FOREIGN PATENT DOCUMENTS

| CH | 346971 | 6/1960 |
| DE | 197 15 724 | 10/1998 |
| EP | 0663197 | 7/1995 |
| WO | WO 81/01098 | 4/1981 |

*Primary Examiner*—Michael A. Brown
(74) *Attorney, Agent, or Firm*—Katten Muchin Zavis Rosenman

(57) ABSTRACT

A balloon for preparing for and easing human birth, which balloon is located at least partly inside the vagina of the pregnant woman during application, has in the inflated condition an application region (P) between its outer end (A), which is provided with a fitting (1) for a flexible tube, and its vaginal portion with the largest diameter (D); the balloon is conically shaped in its application region (P); the application region (P) is disposed approximately within the middle third of the balloon length between an outer portion (a) and an inner portion (i) of the balloon; the cone angle β in the application region is 25° or smaller.

Figure 1:
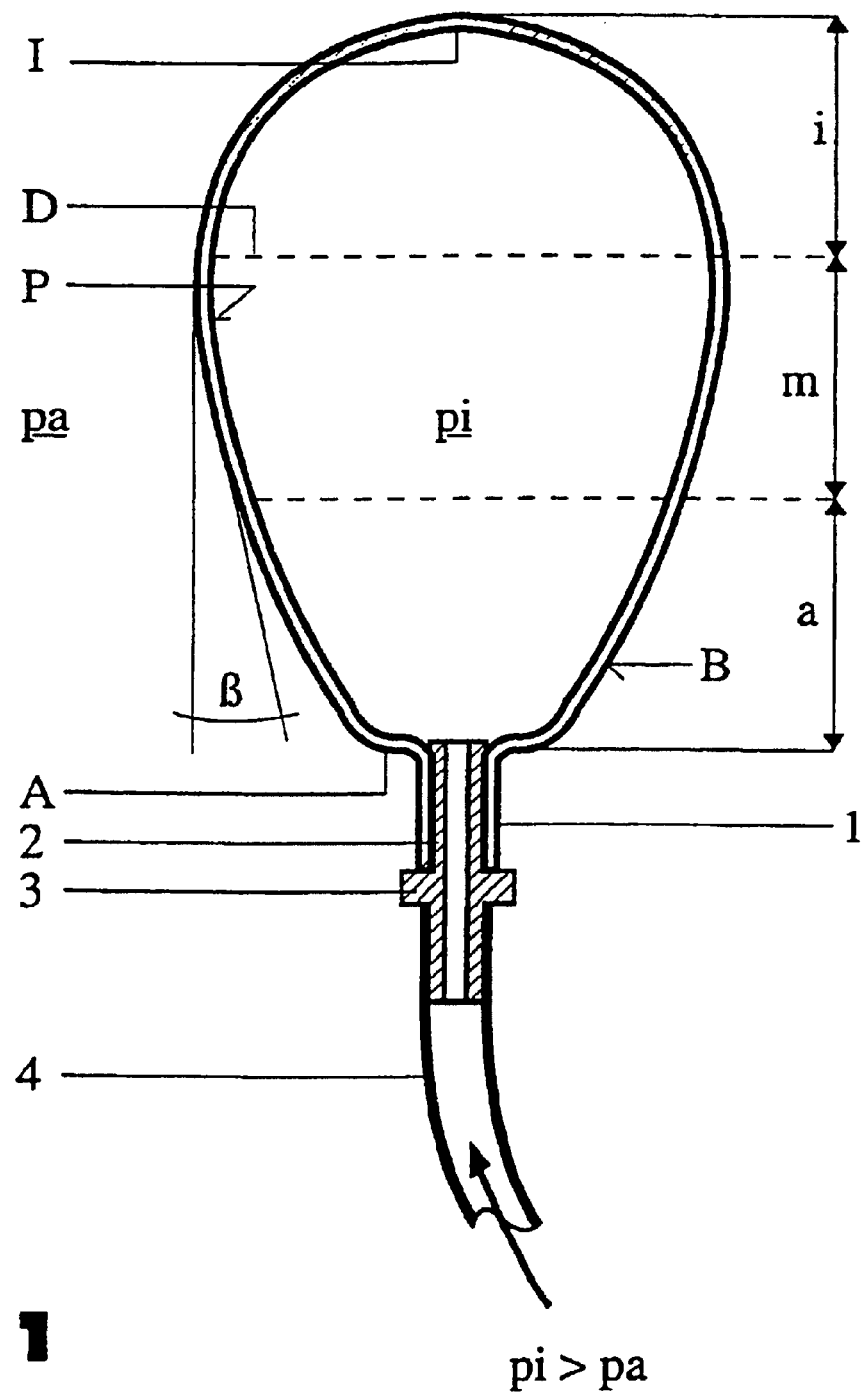

10 Claims, 7 Drawing Sheets pi > pa

BALLOON FOR PREPARING FOR AND EASING HUMAN BIRTH

The invention relates to a balloon for preparing for and easing human birth, which balloon is located at least partly inside the vagina of the pregnant woman during application and which is substantially conically shaped in an application region between its outer, end, which is provided with a fitting for a flexible tube, and its vaginal portion with the largest diameter.

Such a balloon, which in the inflated condition has an elongate form, which is provided in a middle portion with a waist-like constriction, is described in German Unexamined Application 19715724. During application thereof, the waist is disposed in the region of the orifice of the birth canal. By activation of the musculature of the pelvic floor, the pregnant woman can exercise by pushing the balloon out of the vagina in preparation for giving birth, and in this way simulate the process of giving birth. The portion of the balloon section located inside the vagina and tapering conically toward the waist then causes the orifice of the birth canal to dilate in a manner similar to that caused by the emerging head of a baby.

It has been found that the said conical portion is particularly advantageous in connection with the gymnastic effect of the balloon. The object of the present invention is therefore to enhance this effect even more by a suitable configuration of the balloon.

For this purpose it is provided according to the invention that the application region of the balloon adjoins the outer end of the crown region of the balloon in a conical portion, where it extends between an outer portion and an inner portion of the balloon approximately within the middle third of the balloon length, and that the cone angle in the application region is 25° or smaller.

In this connection it is expedient for the cone angle to be between 5 and 15° and the diameter of the balloon in the crown region to be about 9 cm in the inflated condition, and for its length, measured from the inner end to the outer end of the application region, to be 10 to 15 cm.

In a balloon with such a configuration, there is provided a conical face that is much longer than in the known balloon and that extends at least over the entire application region thereof, the said region representing approximately the middle third of the total balloon length. The outer portion of the balloon adjoining the outer end of the said middle third represents approximately the outer third of the balloon and expediently is also conically formed, such that it continues the cone of the application portion in the direction of decreasing diameter. Upon commencement of the gymnastic exercises, this conical outer portion then has the effect that it leads gently to a steadily increasing extension effect during the pushing exercises and thus ensures almost painless progressive increase of the intensity of the exercise.

In order not to endanger the mouth of the womb, it is advisable that the part of the balloon located inside the vagina have a length of less than 15 cm in the inflated condition. In the maximally inflated condition, its largest diameter in the crown region between the application portion and the inner portion is 9 to 10 cm, corresponding to the size of the head of a baby at birth.

The different methods for achieving the conical form of the balloon are evident from the embodiments of the empty balloon envelope or the just-inflated balloon envelope specified in the dependent claims, the internal pressure of the balloon corresponding to or being slightly higher than atmospheric pressure.

In principle, the shape of the balloon in the inflated condition can be achieved either by an appropriate variation in wall thickness along a substantially cylindrical balloon shape or by a corresponding conical envelope shape. In the first case, it is essential that the envelope wall thickness decrease in the direction of increasing balloon diameter; in the second case, the cone angle of the envelope should be approximately equal to that of the inflated balloon.

Finally, the shape of the inflated balloon can also be achieved by appropriate pre-stretching of the balloon. Because of the associated overextension effect or of the distention of the envelope material beyond the reversible limit of elasticity caused by stretching, preferential extension within the stretched portions takes place during subsequent inflation, and so any desired cross-sectional configurations expanding in the manner of a conical shape can be achieved.

The cone angle of the inflated balloon should preferably be smaller than 25°. In practice, exercising subjects have found an angle of about 10° to bee an agreeable value, at which overextension of the muscle tissue is simultaneously avoided.

As material for the balloon there are preferably used thermoplastic elastomers or silicone rubbers, which have a favorable combination of mechanical characteristics, material resistance and biocompatibility. Polyvinyl chloride is also suitable.

Figure 2:
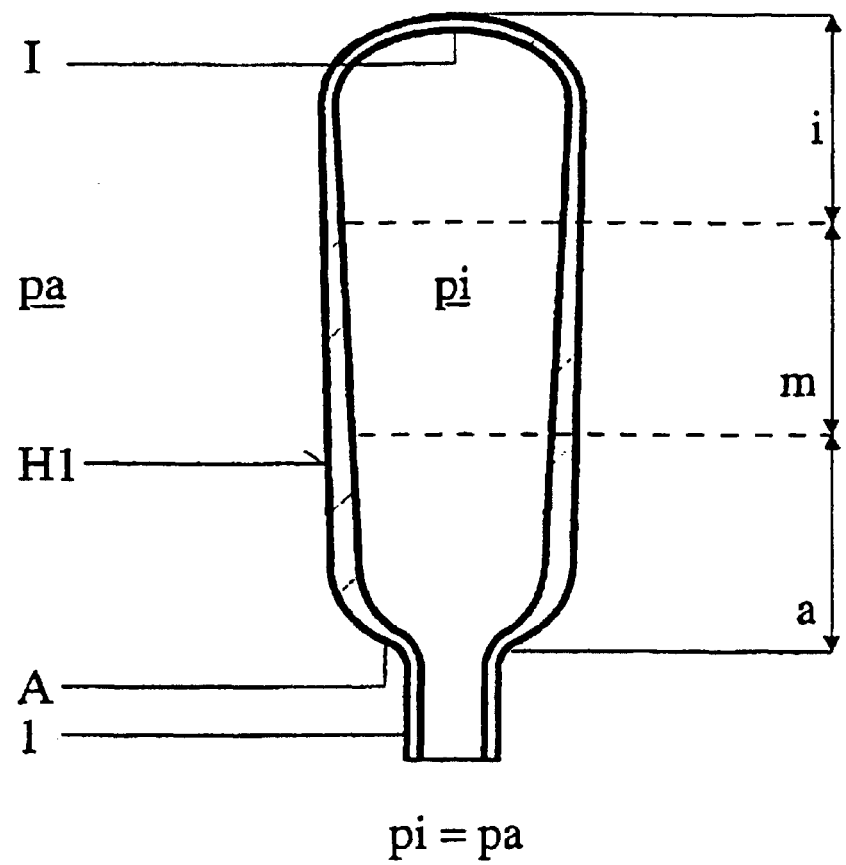
Figure 3:
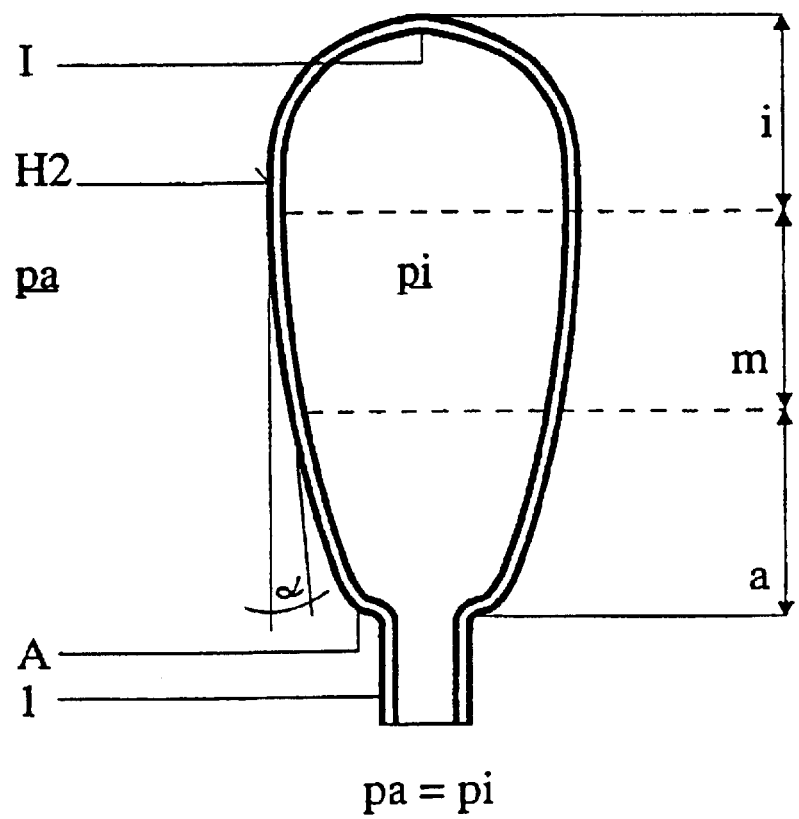
Figure 4:
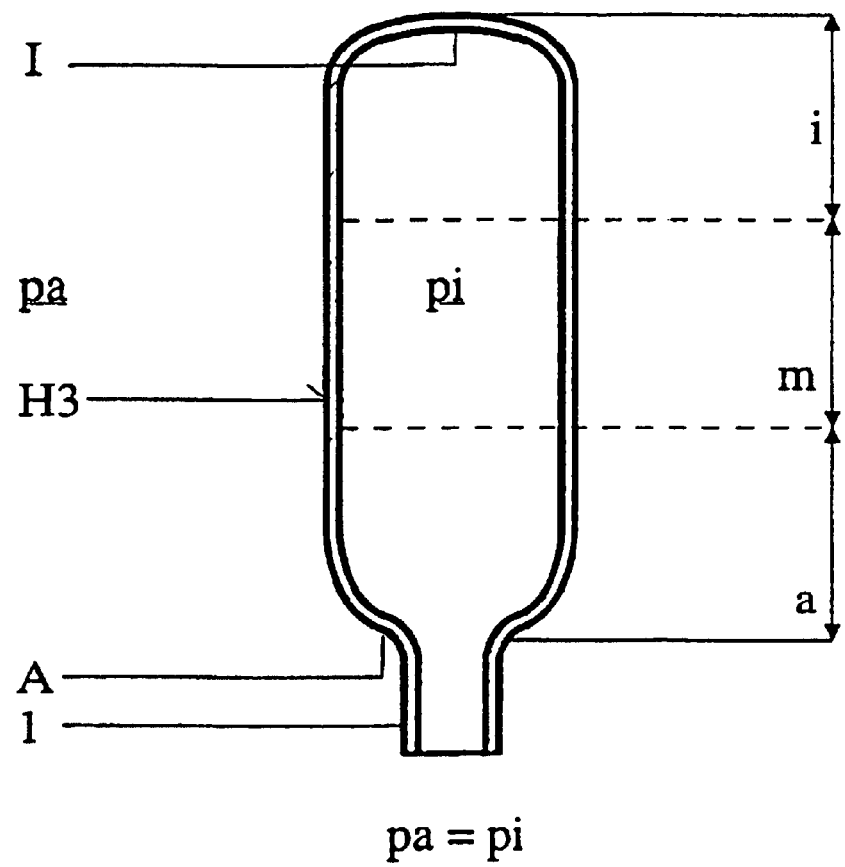
Figure 5:
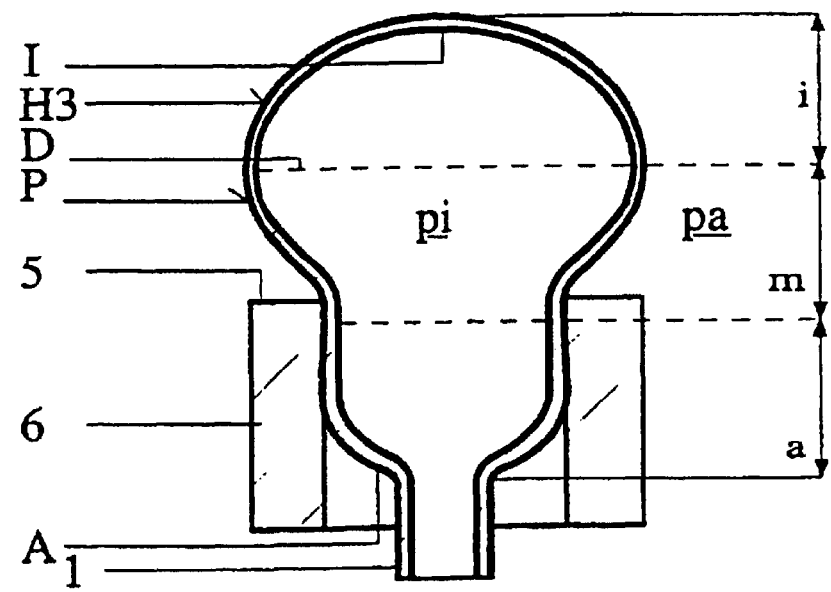
Figure 6:
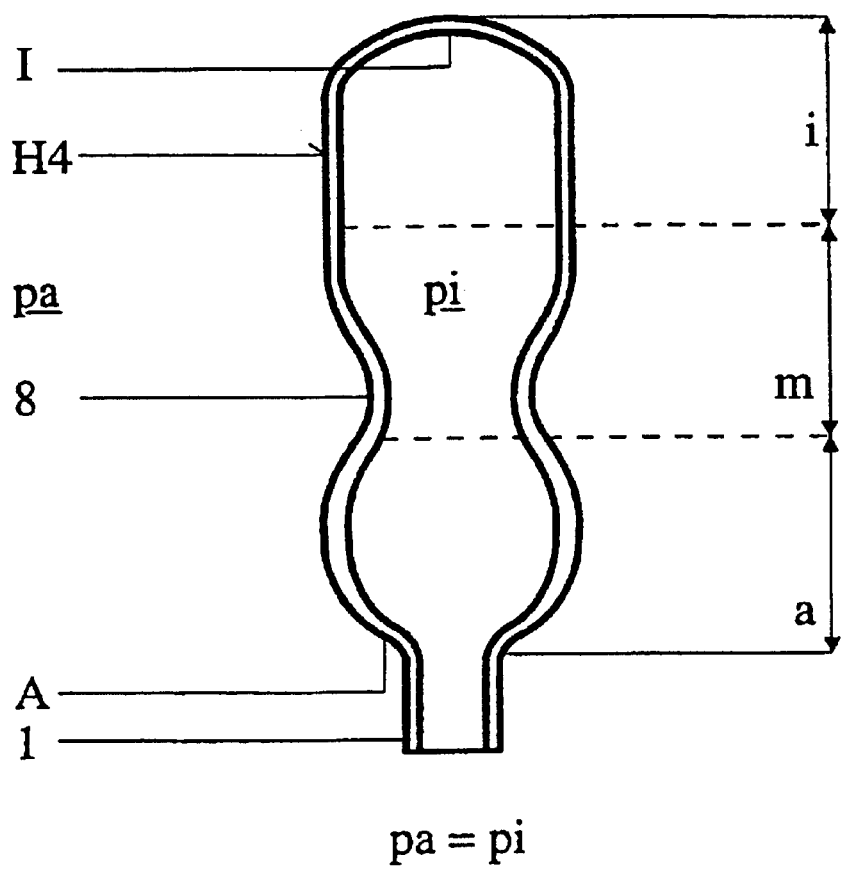
Figure 7:
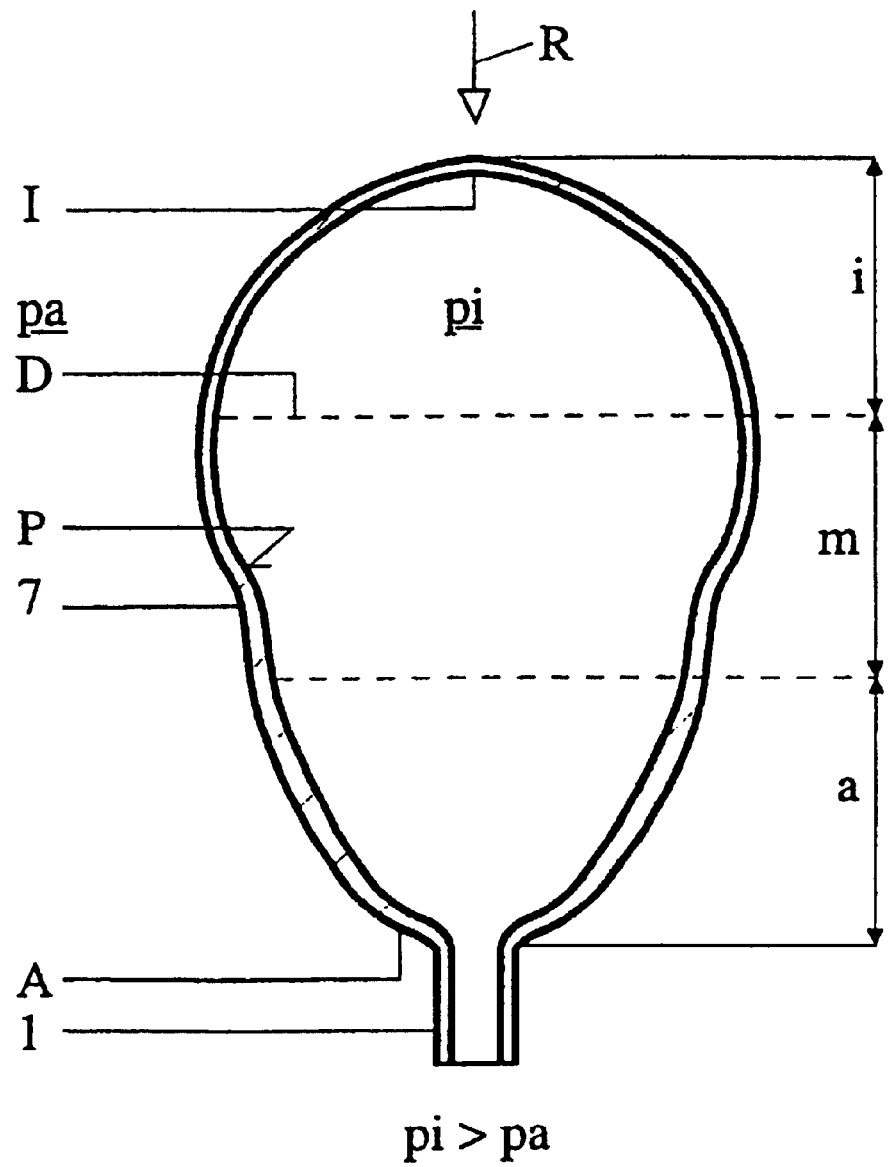

The invention will be explained hereinafter on the basis of several practical examples, wherein FIG. 1 shows a longitudinal section through an inflated balloon, FIG. 2 shows a longitudinal section through a balloon envelope with different wall thicknesses, FIG. 3 shows a longitudinal section through a conically preformed balloon envelope, FIGS. 4 and 5 show envelope and balloon with stretched middle portion, FIGS. 6 and 7 show a waisted balloon envelope and balloon.

FIG. 1 shows a longitudinal section through an inflated balloon B. In this condition its internal pressure $p_i$ is higher than its external pressure $p_a$. In its maximally extended final form, balloon B has a largest diameter D of 9 to 10 cm, corresponding to the size of a baby's head. Its length from its inner end I to its outer end A is approximately 20 to 24 cm in the fully inflated condition. The overall length of balloon B is divided into three portions, each amounting to about one third of its length, namely an inner portion i between its crown region with the largest diameter D and inner end I; a middle portion m between its inner portion i and an outer portion a, the said middle portion m having substantially conical shape and corresponding to application region P of balloon B; outer portion a extends from middle portion m to outer end A of balloon B; as shown in FIG. 1 it is also conical, specifically forming a continuation of the conical shape of middle portion m. At its outer end A, balloon B has a connecting fitting 1 in the form of a flexible tube, stiffened by a tubular insert 2. At approximately the midpoint, tubular insert 2 has a shoulder 3, on the opposite sides of which there are attached connecting fitting 1 of balloon B and the end of a flexible tube 4, which places balloon B in communication with an inflation device (not illustrated), such as a hand pump.

During application for the purpose of prebirth gymnastics, the pregnant woman inserts the deflated balloon B into the vagina, after which she pumps it up to an increasing degree corresponding to the progress of training and, with end A located outside the vagina, presses against the vaginal orifice by exerting the musculature of the pelvic floor and the vaginal musculature. In the process, the conical form of balloon B causes, in the region of its application portion P, increasing dilation of the orifice of the birth channel. For this purpose a suitable cone angle for the balloon shape is smaller than 25°, preferably between 5 and 15°, ideally about 10°.

FIG. 2 shows a longitudinal section through a marginally inflated but not expanded balloon envelope H1, wherein the internal pressure $p_i$ corresponds approximately to the external pressure $p_a$. The cylindrical circumferential wall of balloon envelope H1 is formed such that its wall thickness decreases from outer end A to inner end I. If balloon envelope H1 is inflated, the balloon becomes conically shaped over its entire length, with diameters increasing from outer end A to inner end I. In this case, the crown region of the balloon with the largest diameter D is closer to inner end I than in the embodiment according to FIG. 1.

FIG. 3 shows a cross section through an elongate balloon envelope H2, which is substantially conically shaped over the entire length, with a cone angle α of about 5 to 10°. The diagram according to FIG. 3 shows balloon envelope H2 with $p_i=p_a$, or in other words with equal pressures inside and around the balloon envelope. Balloon envelope H2 has constant wall thickness over the entire cross section. Because of its conical initial shape, it yields a balloon shape corresponding approximately to that of FIG. 1 when in the inflated condition.

Despite different initial parameters, therefore, balloon envelopes H1 and H2 according to FIGS. 2 and 3 therefore achieve very similar balloon shapes when measured in their inflated condition in which $p_i > p_a$.

FIG. 5 shows a partly inflated balloon envelope H3, wherein the envelope is being stretched in the region of its middle portion, such that a conically shaped application region P is formed between its crown region with the largest diameter D and the upper end 5 of a retaining ring 6. The initial shape of envelope H3 is illustrated in FIG. 4, where $p_i=p_a$. In a manner similar to the embodiment according to FIG. 2, it is cylindrical over the entire length but, in contrast to FIG. 2, it has constant wall thickness, corresponding to the conical envelope H2 illustrated in FIG. 3. By stretching envelope H3 in application region P, to produce the desired conical shape there when the balloon is inflated, there is no need to make an envelope with variable wall thickness, thus simplifying production. The stretching process also opens up the possibility of adjusting the cone angle β in application region P to a value that can be selected between wide limits. Once the envelope material has been stretched according to FIG. 5, the final balloon shape obtained upon inflation of envelope H3 without the retaining form shown in FIG. 5 once again corresponds substantially to that of FIG. 1. Thus, as was already the case for the versions according to FIGS. 2 and 3, there is no need to illustrate it.

An embodiment of a balloon whose shape differs slightly from that of the balloon according to FIG. 1 is illustrated in FIG. 7. Therein a slight constriction 7 is visible in application region P, which corresponds to middle portion m. This is caused by the waist 8 present in the middle portion of the associated envelope H4 shown in FIG. 6. The approximately conical shape that the inflated balloon shown in FIG. 7 has overall in the region of its middle portion m and of its outer portion a results from a larger wall thickness of envelope H4 in the region of its outer and middle portions, compared with its inner, approximately cylindrical portion, formed with constant wall thickness.

In the embodiment of the balloon according to FIG. 7, its constriction 7 produces, during application, an increased resistance in expulsion direction R because of the slight constriction 7 in the transition region from conical shape to inner portion i, or in other words to the crown region of the balloon characterized by the largest diameter D. Thus this balloon shape makes it possible to establish a specified pressure point during expulsion of the balloon from the birth canal by the musculature of the pelvic floor and vaginal musculature of the woman, similar to the increased resistance upon penetration of the baby's head through the orifice of the birth canal.

Furthermore, in the embodiment according to FIGS. 6 and 7, the positioning of envelope H4 is particularly simple, in that it is sufficient at first to introduce envelope H4 as far as waist 8 into the vagina. With increasing inflation of the balloon, waist 8 then shifts further inward, so that application region P of the balloon illustrated in FIG. 7 is located immediately inside the vaginal orifice, whereas outer portion a of the balloon is located outside the vagina.

What is claimed is:

1. A balloon for preparing for and easing human birth, which balloon is located at least partly inside the vagina of the pregnant woman during application and which is substantially conically shaped in an application region (P) between its outer end (A), which is provided with a fitting (1) for a flexible tube, and its vaginal portion with the largest diameter (D), wherein the application region (P) of the balloon adjoins the outer end of the crown region of the balloon in a conical portion, where it extends between an outer portion (a) and an inner potion (i) of the balloon approximately within the middle third of the balloon length, and in that the cone angle (β) in the application region is 25° or smaller.

2. A balloon according to claim 1, wherein the cone angle (β) is between 5 and 15° when the balloon is inflated.

3. A balloon according to claim 1, wherein, in the inflated condition, its diameter (D) in the crown region is about 9 cm and in that its length, measured from the inner end to the outer end of the application region (P), is 10 to 15 cm.

4. A balloon according to claim 1, wherein its unpressurized envelope (H1) has a wall thickness that decreases from outside to inside, at least the the application region.

5. A balloon according to claim 4, wherein its unpressurized envelope (H1) has a cylindrical shape when the external and internal pressures are equal, and in that the wall thickness of the envelope (H1) decreases from outside to inside.

6. A balloon according to claim 1, wherein its unpressurized envelope (H2), measured in the pressure condition of equal external and internal pressures, has a conical shape corresponding to the application region (P).

7. A balloon according to claim 1, wherein its unpressurized envelope (H3) is pre-stretched in the application region (P), such that the application region (P) assumes, in the inflated condition of the balloon, a shape that flares from its outer portion (a) to its inner portion (i).

8. A balloon according to claim 1, wherein its unpressurized envelope (H4), measured in the pressure condition of equal external and internal pressures, is constricted in the form of a waist in the application area (P), and in that the wall thickness in the outer portion of the envelope (H4) adjoining the waist (8) is larger than in the application area (P).

9. A balloon according to claim 1, further comprising a connecting fitting (1) in the form of a flexible tube molded onto its outer end (A) and stiffened by a tubular insert (2).

10. A balloon for preparing for and casing human birth, which balloon is located at least partly inside the vagina of the pregnant woman during application and which is substantially conically shaped in an application region between its outer end and its vaginal portion with the largest diameter, wherein the application region of the balloon adjoins the outer end of the crown region of the balloon in a conical portion, where it extends between an outer portion and an inner portion of the balloon approximately within the middle third of the balloon length, and in that the cone angle in the application region is 25° or smaller, and wherein, in the inflated condition, its largest diameter in the crown region is about 9 cm and in that its length, measured from the inner end to the outer end of the application region, is 10 to 15 cm.

* * * * *